United States Patent [19]
Kullas et al.

[11] Patent Number: 6,077,246
[45] Date of Patent: Jun. 20, 2000

[54] MEDICAL IRRIGATION PUMP AND SYSTEM

[75] Inventors: Karen E. Kullas, Taunton, Mass.; Glen French, Barrington, R.I.; Joan Kinniburgh, Braintree, Mass.; Augustus Felix; Philip Tessier, both of Cranston, R.I.; Dean L. Kamen, Bedford, N.H.; Bradley Miller, Londonberry, N.H.; Kevin Grant, Manchester, N.H.

[73] Assignee: DEKA Products Limited Partnership, Manchester, N.H.

[21] Appl. No.: 09/362,946

[22] Filed: Jul. 28, 1999

(Under 37 CFR 1.47)

Related U.S. Application Data

[62] Division of application No. 08/698,568, Aug. 15, 1996, abandoned.

[51] Int. Cl.[7] .................................................. A61M 1/00
[52] U.S. Cl. ......................... 604/151; 417/477.2; 604/65
[58] Field of Search ................................... 604/151, 153, 604/27, 29, 30, 152, 49, 51, 65–67, 118–120, 123, 131, 156; 128/DIG. 12, DIG. 13; 417/477.2

[56] References Cited

U.S. PATENT DOCUMENTS

| | | | |
|---|---|---|---|
| 2,773,453 | 12/1956 | Gemeinhardt | 103/83 |
| 3,927,955 | 12/1975 | Spinosa et al. | 417/477 |
| 4,537,561 | 8/1985 | Xanthopoulos | 417/477 |
| 4,635,621 | 1/1987 | Atkinson | 128/66 |
| 4,940,457 | 7/1990 | Olson | 604/30 |
| 4,986,821 | 1/1991 | Kamen | 604/251 |
| 5,178,515 | 1/1993 | Tsuchiya et al. | 415/206 |
| 5,246,422 | 9/1993 | Favre | 604/110 |
| 5,431,627 | 7/1995 | Pastrone et al. | 604/65 |
| 5,460,490 | 10/1995 | Carr et al. | 417/44.2 |
| 5,464,391 | 11/1995 | De Vale | 604/67 |
| 5,554,155 | 9/1996 | Thomas et al. | 604/65 |
| 5,647,852 | 7/1997 | Atkinson | 604/151 |
| 5,800,396 | 9/1998 | Fanney et al. | 604/151 |

FOREIGN PATENT DOCUMENTS

| | | |
|---|---|---|
| 0 293 592 A2 | 12/1988 | European Pat. Off. . |
| WO 96 34205 | 10/1996 | WIPO . |

*Primary Examiner*—Wynn Wood Coggins
*Assistant Examiner*—Sharon Finkel
*Attorney, Agent, or Firm*—Bromberg & Sunstein LLP

[57] ABSTRACT

A medical irrigation pump and pump system utilize a permanent non-sterile drive motor capable of operating disposable sterile single use pump units each of which is specifically designed for a particular medical procedure. The pump units have housings which are adapted to be interchangeable within the permanent controller system. Only the sterilized and disposable pump units come into contact with the fluid pathway during pumping. A pattern of bumps on each pump unit is unique for the medical procedure for which the pump unit was designed. The pattern of bumps engages switches on the controller, enabling the controller to identify what type of pump unit has been installed. After automatically identifying the type of pump unit and the intended medical procedure, the controller automatically selects a default motor speed that will provide an appropriate fluid pressure for that particular procedure. Buttons on a control panel also enable the user to manually adjust the pressure delivered by the pump. The orientation of the pump unit during the loading procedure allows easy purging of all air from the pump unit before the pump is started.

22 Claims, 12 Drawing Sheets

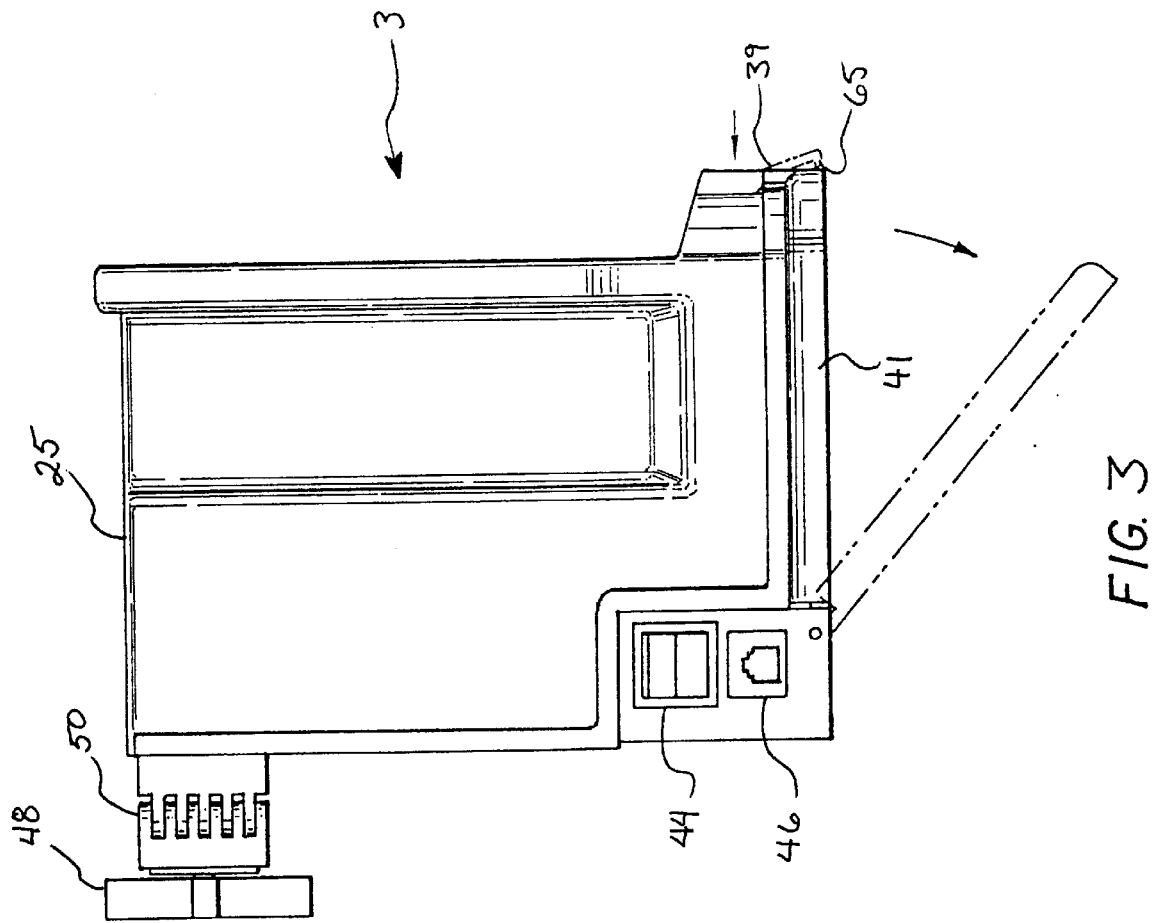
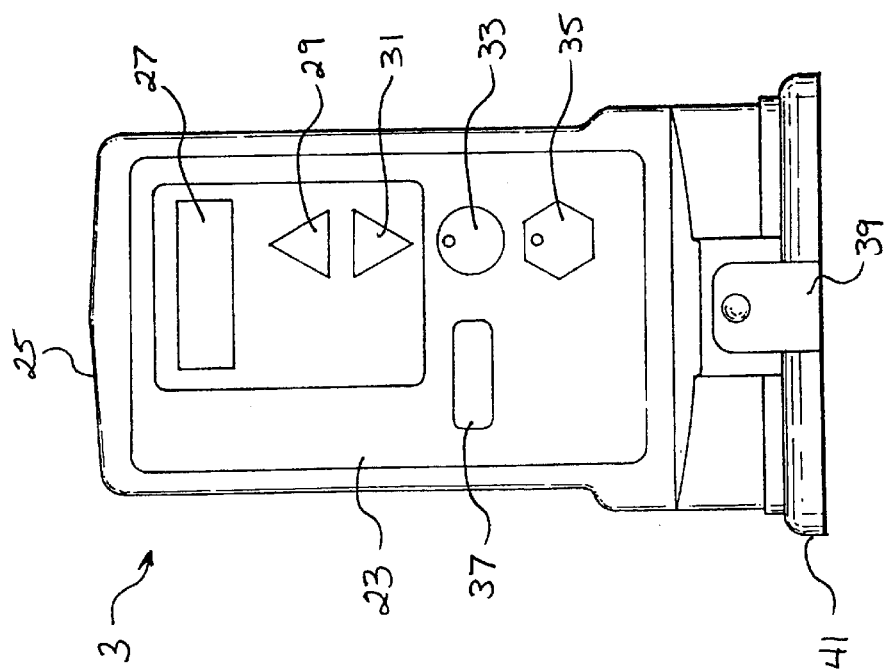
FIG. 3
FIG. 2

MEDICAL IRRIGATION PUMP AND SYSTEM

RELATED U.S. APPLICATION(S)

The present application is a divisional application of U.S. application Ser. No. 08/698,568, filed on Aug. 15, 1996, now abandoned, which is hereby incorporated herein by reference.

FIELD OF THE INVENTION

This invention relates to irrigation pump systems, particularly to devices used to irrigate surgical sites during medical procedures.

BACKGROUND OF THE INVENTION

Devices that deliver irrigating fluid to an irrigation site are necessary in a variety of medical and dental procedures. For example, laparoscopic, arthroscopic and hysteroscopic procedures require sufficient volumes of irrigation fluid to be delivered to the surgical site in order to maintain tamponade, isolate bleeders and to generally clear the surgical area. Laparoscopic procedures involve incisions to the abdominal cavity and include appendectomies, cholecystectcomy (incision of the gall bladder) and treatment of ectopic pregnancies. Hysteroscopic procedures involve inspection of the uterine cavity and include procedures that remove abnormal tissue from the uterus such as a biopsy or a myomectomy. Arthroscopic procedures are typically performed by an orthopedic surgeon and involve irrigation, distension and inspection of the joints such as at the knee, shoulder, elbow or ankle. Such arthroscopic procedures include synovectomy, meniscectomy or repair of the anterior cruciate ligament.

During these various medical procedures, it is generally useful for the surgeon to keep tissue that surrounds the surgical site out of the way by injecting solutions such as saline, glycine or lactated ringer's solution into the subject area. As each procedure different volumes of fluid delivered at various pressures, it would be useful for health care providers to have a single pump that could be adapted to deliver the appropriate irrigation for various procedures.

Another important aspect of medical irrigation pumps is sterility. Fluid that enters the body during a surgical procedure must be maintained sterile. However, efforts to maintain sterility become complicated when expensive hardware, such a s a pump, is used. Sterility is more easily and assuredly maintained when medical devices that carry irrigant fluid to the body can be discarded after each use. It is possible to provide a medics irrigation pump that utilizes a permanent non-sterile pump motor that can generate pumping action in a sterile fluid pathway that is disposable and detachable from the permanent motor hardware.

U.S. Pat. No. 3,927,955 (Spinosa et al.) discloses a medical cassette pump that utilizes peristaltic pumping action to pump fluid through a sterilized fluid path. The pump consists of a non-sterile permanent electric motor that rotates planetary rollers. The rollers engage the exterior surface of flexible sterilized tubing that is maintained around the circular outer edge of a disposable cassette. As the rollers compress the tubing against the edge of the cassette, fluid pumping action is provided. The cassette and tubing are removable from the rollers and motor and may be discarded and replaced with a now sterile cassette and tube for each use.

U.S. Pat. No. 4,635,621 (Atkinson) discloses a lavage pump system that utilize s a permanent electric motor that engages a sterile disposable pumping unit. A linear reciprocating electric motor releasably engages the end of a piston rod that is part of the piston/cylinder disposable pump. The replaceable sterile lavage pump slides into a compartment that is adjacent the electric motor so that the motor and piston rod can be maintained in a working relationship. It would be highly desirable to provide a medical pump that could drive a wide variety of sterile replaceable pumping mechanisms to serve the many medical procedures that health care providers must perform,

SUMMARY OF THE INVENTION

This invention relates to fluid pumps used in medical procedures that employ a permanent non-sterile pump motor which interfaces with a sterile and disposable pumping mechanism and fluid pathway. This pump system utilizes a sophisticated electronic controller that powers a rotary electric motor. The controller and motor are provided with a holder that is designed to receive one of several disposable and sterile pumping mechanisms or bodies that join and become part of a sterile fluid pathway through which the irrigation fluid travels. Sterile irrigation fluid may be supplied from irrigation bags or bottles to the pump body through flexible tubing. After the irrigation fluid is pumped through a sterile pump body it travels out through flexible tubing to an irrigation handpiece that is appropriate for the procedure being performed. All components of the fluid pathway (irrigant bags, pump body, handpiece and flexible tubing that joins them) are sterile, disposable single use items.

Several distinctly configured pumping mechanisms or pump bodies can be used with the motor/controller system. A centrifugal pump utilizing a spinning impeller to create a controlled fluid pressure and flow rate is used in laparoscopic, hysteroscopic and arthroscopic procedures. However, as each procedure requires a specific fluid delivery pressure and rate, three different pump types utilizing respectively sized impellers are used. Other pumping mechanisms can also be used with the controller; these pumping mechanisms can also be configured to generate fluid outputs which are specifically suited for a particular medical procedure.

The permanent controller is capable of receiving the various disposable pump body types in a specially-shaped holder attached to the bottom of the controller. More particularly, a frame hinged along the back edge of the bottom of the controller is opened and tilted downward to receive the disposable pump body. Although each pump body type has a different internal configuration suitable for its intended procedure, the external dimensions of all pump body types are the same so that each pump body will fit in the controller frame. Once the pump body has been placed into the lowered frame, the frame is closed upward and latched so that the pump body engages the controller and drive motor.

The pump body interfaces with the controller in several ways. First, the pump motor engages the pump drive member of the disposable pump. A paddle attached to the end of the rotating motor shaft catches and rotates a pump drive rod that protrudes through the top of the pump body. Thereafter, when the electric motor rotates, the rotating paddle will cause the pumping mechanism to rotate, in turn, generating a fluid flow through the given pump body and delivering a fluid output at a controlled pressure. The fluid delivery rate and pressure can be changed, within limits determined by the pump body design, by increasing or decreasing the rotational speed of the motor.

The disposable pump body interfaces with the controller in a second manner that enables the controller to automatically identify which type of pump body has been inserted and, based on that identification, to set an initial default motor speed and upper and lower motor speed limits to the appropriate levels. This identification is accomplished by switches located at the interface between the controller and the pump body, switches detect which pump body type has been installed in the controller. In particular, small bumps molded into the top of each pump body in a pattern unique to each pump body type engage an array of switches which is located on the underside of the controller. When the hinged frame is closed to engage the pump body with the controller, the bumps operate the switches in a predetermined pattern unique to that particular pump body. The pattern of depressed switches is used to retrieve identification information and default settings from a non-volatile storage located in the controller. The retrieved information is used to drive an LED display that notifies the user as to which pump body type has been installed by displaying a medical procedure type that corresponds with the installed pump body type (for example, a laparoscopic procedure, hysteroscopic procedure, arthroscopic procedure, etc.) As a safety feature, the user must confirm that the displayed procedure type is the intended procedure by pressing a confirmation button before the pump will start. Upon confirmation by the user, the controller selects a default motor speed that will generate an appropriate fluid pressure and subsequent flow rate for the given procedure. Upper and lower speed limits are also retrieved from the internal storage to set the maximum and minimum fluid pressures, respectively.

A user can easily set-up and operate the desired irrigation pump, with a minimum of preparation time when using this system. Upon selecting the appropriate pump body type for the desired medical procedure, the user simply joins a reservoir of irrigation fluid such as saline, lactated ringer's or glycine to the pump body via flexible tubing. The reservoir is mounted above the pump body to promote fluid flow by gravity into the pump. The user may also install an appropriate irrigation handpiece to the pump outlet via flexible tubing. The flexible tubing set may be provided with a preconnect end fitting for quick connection to medical devices which attach to the patient. To install the pump body into the controller, the user releases a catch on the front of the frame which is hinged at the opposite side and swings downward in the front. The user then inserts the pump body into the frame.

While resting in the inclined open frame, the pump body fills with fluid and air is automatically purged from the pump body to prime the pump. The angled position of the pump body in the open frame insures that any air in the pump body is driven out as the pump body fills with fluid due to the relative positions of the fluid inlet and outlet lines. Specifically, the outlet line which is located at the bottom of the pump body at a position near the frame hinge is connected to a channel molded into the interior of the pump body which insures that the fluid outlet is located at the top of the pump body. Therefore, fluid entering through the inlet line at the center of the pump body (carried by gravity) fills the pump body and air bubbles are pushed to the top of the container and are automatically purged out through the outlet.

After priming is complete, the user closes the frame, engaging the pump with the paddle which is attached to the shaft of the electric motor in the controller. The controller automatically recognizes the type of pump body installed, generates a display indicating the procedure for which the pump body was designed and waits for the user to confirm the procedure. After confirmation, the controller automatically registers a maximum, minimum and default pump pressure and the user may begin the procedure by pressing another controller button to start the controller motor. Once the pump has started, the user may adjust the fluid pressure delivered by the pump at the control panel of the controller by appropriately pressing increase and decrease buttons or may stop the electric motor by pressing a stop button.

It is among the general objects of this invention to provide a medical irrigation pump system that utilizes permanent non-sterile pump motor hardware and a replaceable pump mechanism that is sterile and disposable along with all the components that comprise the fluid pathway.

Another object of the invention is to provide a medical irrigation pump system that can be adapted to be used in various medical procedures requiring various irrigation flow and pressures.

Another object of the invention is to provide a medical irrigation pump system that utilizes a controller that is capable of recognizing and identifying different pumping mechanisms that have been installed for use in various medical procedures.

It is a further object of the invention to provide a pump controller that upon identifying which type of pump mechanism has been installed, automatically sets an appropriate motor speed to drive the pump mechanism safely for the intended procedure.

It is a further object of the invention to provide a pump motor controller that can be adjusted by the user to increase the pump pressure of the irrigation fluid by regulating the motor speed.

It is another object of the invention to provide a medical irrigation pump system that permits quick and easy priming of the installed pump mechanism.

It is another object of the invention to provide various pump mechanisms, suitable for various medical procedures that are easily connectible to conventional irrigation fluid reservoirs and irrigation handpiece assemblies.

BRIEF DESCRIPTION OF THE DRAWINGS

The foregoing and other objects and advantages of the invention will be appreciated more fully from the following further description thereof, with reference to the accompanying drawings wherein:

FIG. 2 is a front view of the irrigation pump controller;

FIG. 3 is a side view of the irrigation pump controller;

DESCRIPTION OF THE ILLUSTRATIVE EMBODIMENTS

Figure 1:
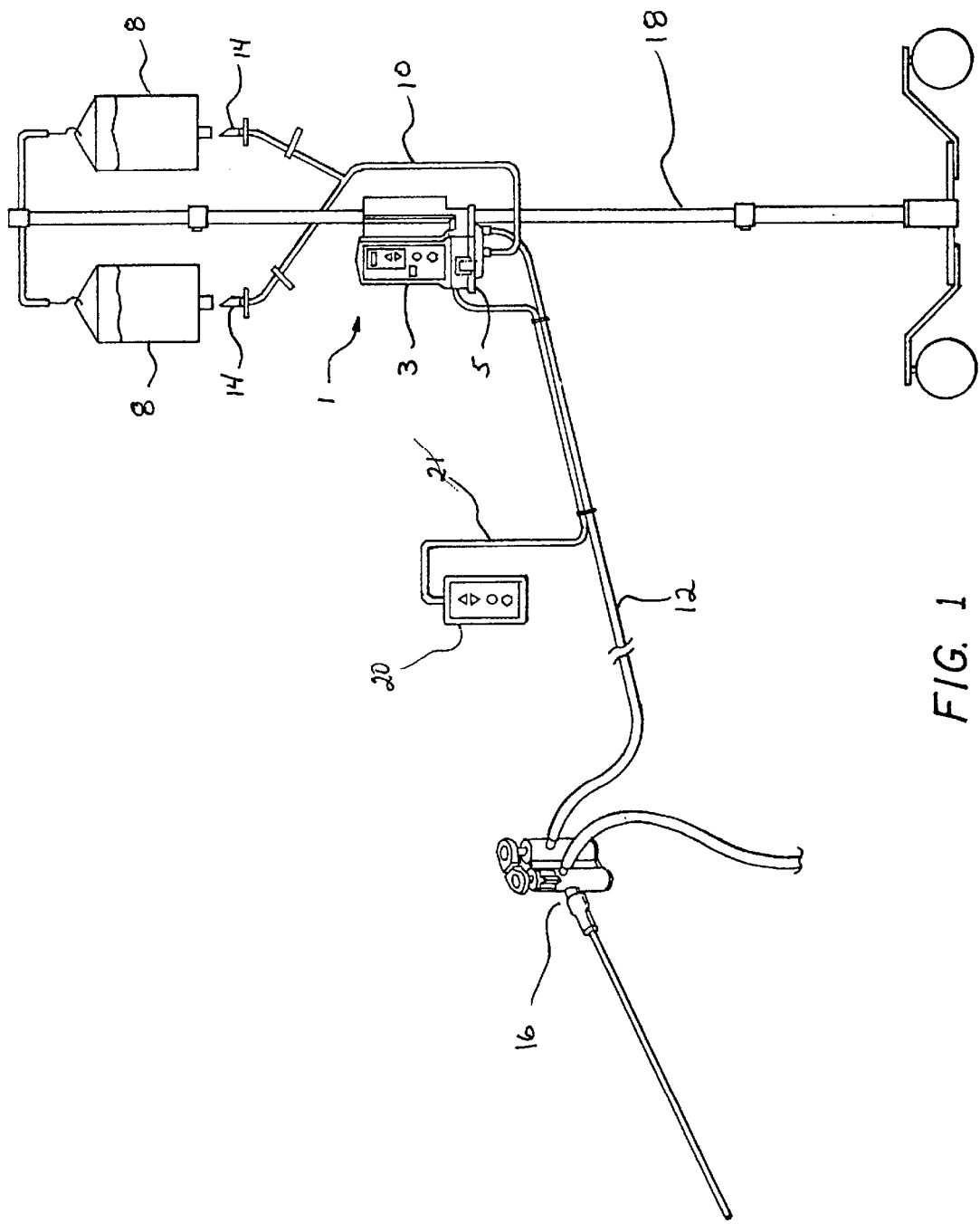
FIG. 1 is a diagram of the irrigation pump system.

FIG. 1 illustrates the irrigation pump system shown generally at 1. In typical use, pump controller 3 with attached pump body 5 can be attached to an I.V. pole 18. In this arrangement, irrigation fluid reservoir bags 8 can be hung above the pump body 5 so that fluid can travel through flexible tubing 10 by gravity to fill the pump 5. Flexible tubing 10 may be joined to the irrigation fluid reservoir bags 8 by inserting bag spikes 14 into bags 8. Pressurized fluid exits the pump body through flexible tubing 12 that is attached to an irrigation handpiece 16 with which the operator can direct the irrigation flow to the surgical site. The irrigation handpiece may also be a simple length of latex tubing.

The controller can be operated by pressing buttons at the front of controller 3 or by using a disposable remote controller unit 20 that is wired to the controller by line 21. It is also possible to control power to the pump through the use of a remotely wired on-off switch located on the irrigation handpiece (not shown).

FIGS. 2 and 3 show the exterior of the irrigation pump controller 3 in more detail. A conventional electric motor with a rotating shaft (not shown) and logic circuitry to control the motor's operation are located within the housing 25 of the controller. A control panel 23, which may be a membrane switch, located on the front of the housing 25 provides the operator with buttons 29, 31, 33, 35 and 37 to operate the pump system. Any or all of the buttons can be provided with an integral LED light which indicates that the function for that button is active. The controller 3 can be mounted to an I.V. pole by clamp 50 which can be tightened or loosened by knob 48. Main power switch 44 and remote controller wire receptacle 46 are located in a recessed portion on the side of the housing 25 to prevent any inadvertent irrigation fluid spills from the reservoir bags 8 from rolling down the side of the housing, seeping into the switches and thereby causing a short circuit or corrosion. Additionally, these electrical components may be covered with elastomeric boots (not shown) to protect them from fluid penetration.

Figure 4:
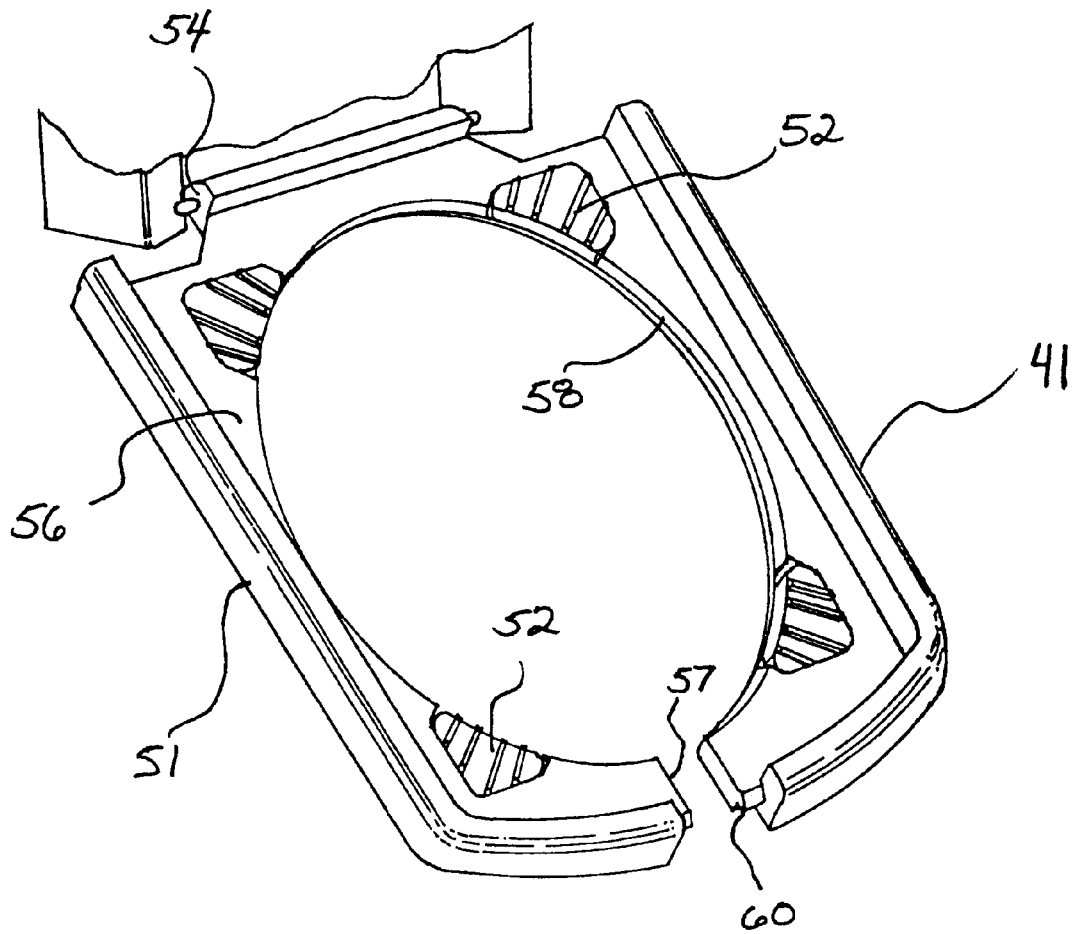
FIG. 4 is a detailed view of the hinged frame of the controller shown in the open position.

At the bottom of the controller housing 25 is a U-shaped frame 41 connected to the controller by a hinge along its back edge 42. FIG. 2 illustrates the controller with the frame 41 in a "closed" or running position whereas FIG. 3 illustrates (in the dotted outline position) the frame 41 in the "open" or priming position. FIG. 4 shows the frame 41, in the open position, attached to the controller housing with rear hinge 54. As shown in dotted outline in FIG. 3, the frame opens to approximately a 45° angle with the horizontal. In the closed position, the frame is maintained in a position substantially flush against the bottom surface of the controller housing 25 by a spring-biased release latch 39. Inwardly projecting hook 65 of release latch 39 catches the front edge of the frame 60 to hold the frame in the closed position. The edge of the latch 39 is designed to allow the door to be angled outwardly then gripped tightly, as both edges of the door engage simultaneously.

Figure 5:
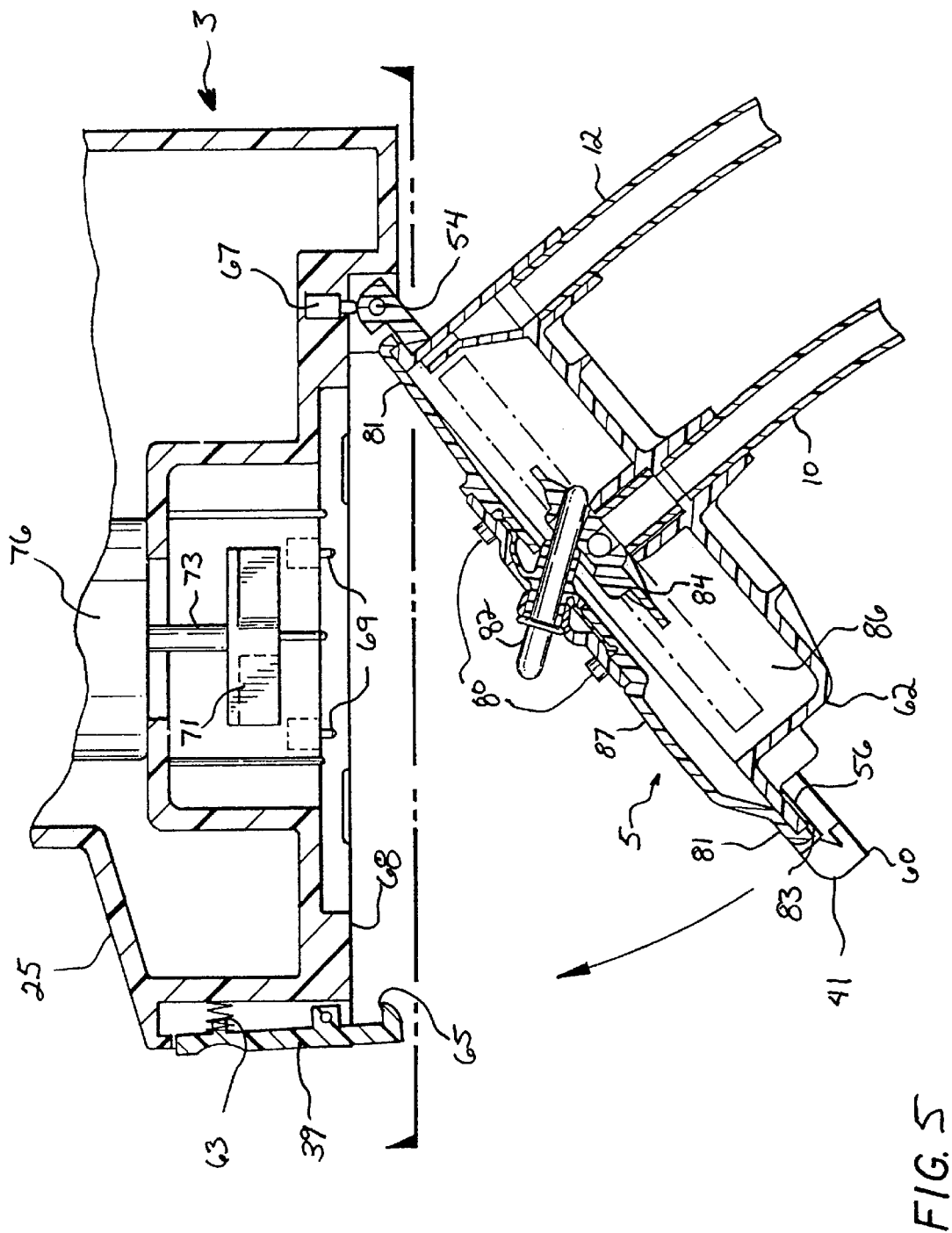
FIG. 5 is a detailed side view of the controller with the hinged frame in the open position and disposable pump body in place.

As shown in FIGS. 4 and 5, the outer edge 51 of frame 41 is contoured to follow the shape of the bottom of the controller housing. However, the inner edge 58 of the frame 41 is contoured to match the exterior shape of a locating ridge on a bowl flange 62 common to all of the various disposable pump bodies 5 that will be used with the controller. Given a circular locating ridge on the cover plate (which locating ridge might comprise the exterior pump body shape in some pump body designs such as that shown in FIG. 5), the inside edge of the frame 41 would also be circular, with a slightly larger diameter, so as to securely hold the pump body. Other pump body shapes, bowl flanges and cover plate ridge shapes could also be used without departing from the spirit and scope of the invention. A shock absorber 67 mounted within the controller housing 25 engages the frame 41 at the location of the hinge 54 to prevent the frame from opening abruptly when button 39 is released and to limit travel of the frame to approximately forty-five degrees from horizontal.

Loading of a pump body 5 is accomplished when the frame 41 is in the open position. Inlet and out lines 10, 12 respectively, that join to the pump body may be passed through a small opening 57 in the frame 41 and the entire pump body 5 may be dropped into the frame from above. The edge 81 of the bowl flange 62 around the outer edge of the pump body contacts the surface 56 of the frame 41 thereby maintaining the pump body at an appropriate depth within the frame. Flexible pads 52 illustrated in FIG. 4 may be positioned at points on the surface 56 of the frame to compensate for any surface imperfections and insure secure placement of the bowl 5 against the bottom surface 68 of the controller housing when the frame is closed. FIG. 5 shows the controller 3 with the frame 41 in the open or priming position with a disposable pump body 5 installed.

Figure 6:
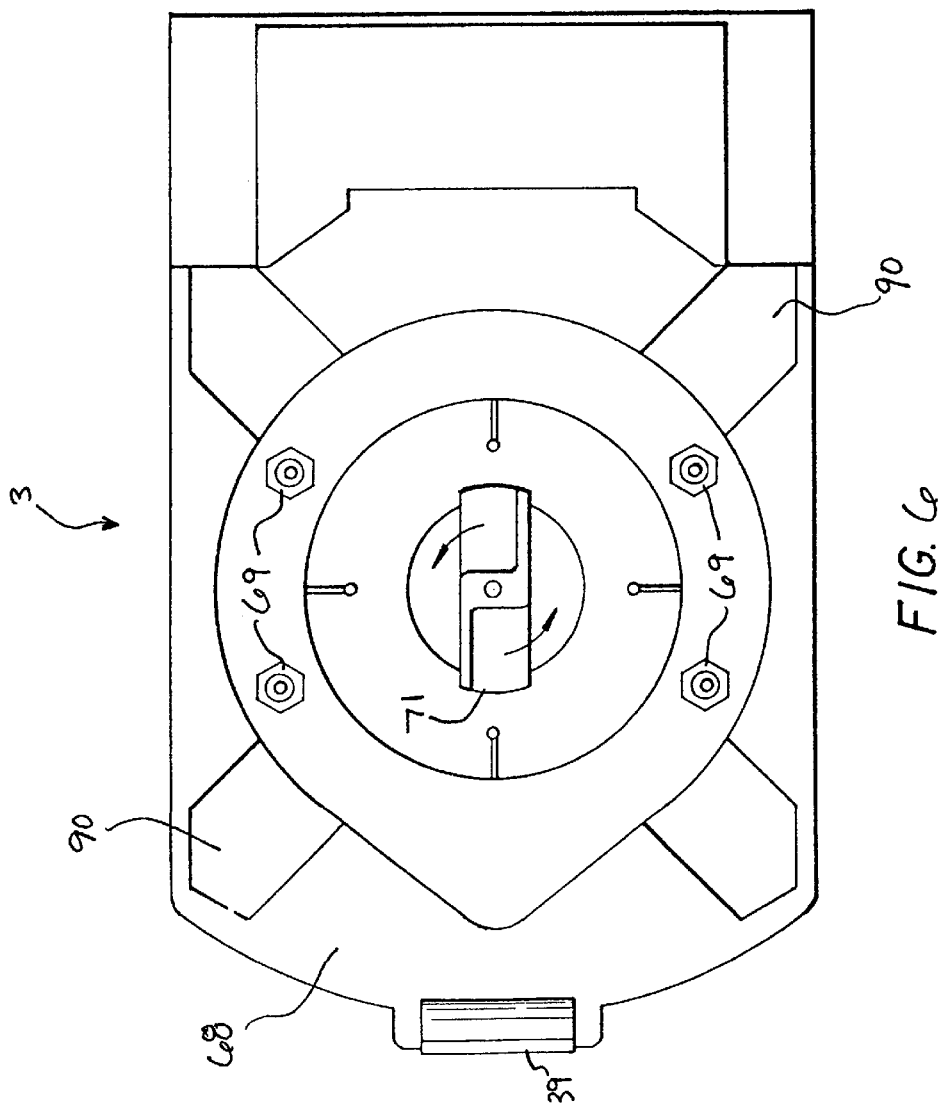
FIG. 6 is a bottom view of the controller (hinged frame not shown for clarity)

Upon closing the frame 41 with pump body 5 loaded, several important interactions occur between the pump body 5 and the undersurface of the controller 3. First, bumps 80 which protrude from the cover plate 87 of the pump body 5 contact and depress one or more switches that are positioned in an array at the undersurface of the controller 3. This switch array is illustrated in FIG. 6 which is a view of the undersurface of the controller housing; the array consists of switches 69. As various pump body types intended for different medical procedures can be placed within the frame 41 and used with controller 3, the controller identifies which body type has been loaded by the pattern of switches 69 that have been depressed.

Figure 8G:
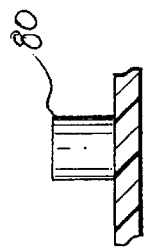
FIG. 8G is a detail of a bump on the top surface of a pump body.
Figure 8C:
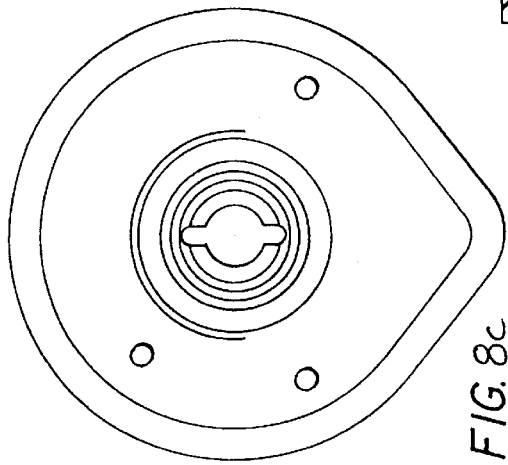
FIGS. 8A–8F are top views of the various pump bodies showing the various sequence of bumps.
Figure 8F:
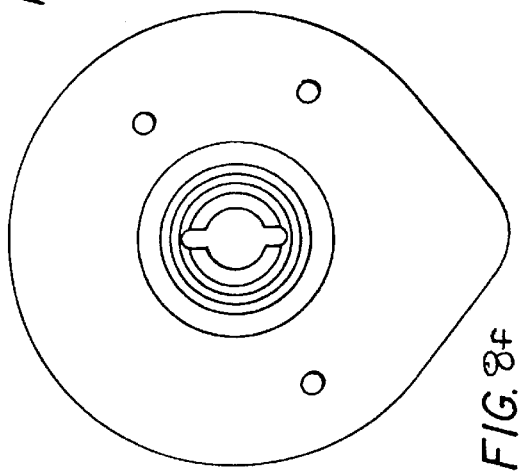
Figure 8B:
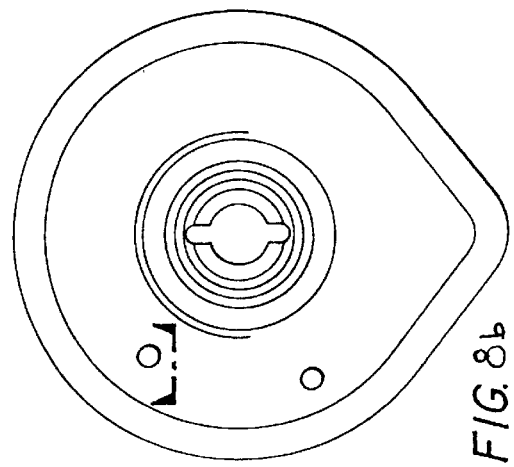
Figure 8E:
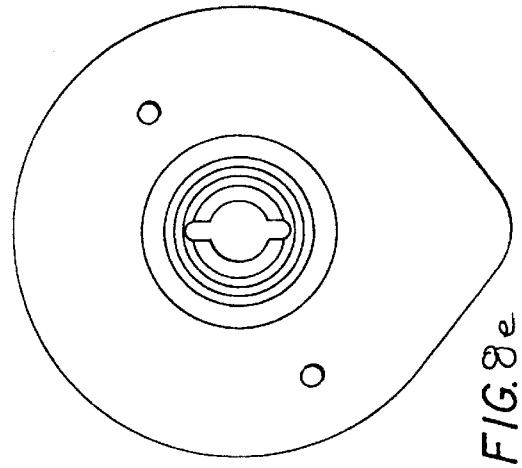

FIGS. 8A–F display the various patterns of bumps that may be molded into the top of the cover plate 87. Six representative patterns are illustrated. These patterns operate with the four position square switch array which is illustrated in FIG. 6, but other numbers of switches can be used without departing from the spirit and scope of the invention. The bumps protrude from the upper surface of the cover plate 87 as shown in the cross sectional view illustrated in FIG. 8G which is a sectional view of the upper bump in FIG. 8B. Each pattern can correspond to a pump body type designed for a particular procedure. For example, the bump pattern illustrated in FIG. 8A may designate a pump body which is designed for use in an arthroscopy procedure. The bump pattern illustrated in FIG. 8B may designate a pump body which is designed for use in a laparoscopy procedure. Other bump patterns can correspond to other procedures and some patterns may be reserved for pump bodies which will be designed in the future. Several illustrative bump patterns are shown in FIGS. 8A–8F; other bump patterns are possible with the four position square array of switches. In addition, other switch arrays can be used in combination with other bump patterns all without departing from the spirit and scope of the invention.

If the presence of a bump represents a logical "1" and the absence of a bump represents a logical "0", then the pattern of bumps represents a binary number. Binary logic within the controller deciphers which pump body type has been installed by reading which switches have been depressed. With this information, the controller then displays on the LED screen 27 the type of procedure for which the installed body is intended. The user then must confirm that this is the intended procedure (that the correct pump body has been installed) by pressing a confirm button 37 located on the control panel 23 of the controller. Thereafter, the controller selects a motor speed that will generate an initial default fluid pressure that is appropriate for that type of procedure. This pressure will be displayed on the LED screen 27. The user then presses the start button 33 to begin pump operation. The pressure may also be modified by the user by depressing increase button 29 or decrease button 31 during operation. To stop the pump, the user presses the stop button 35.

More particularly, the switches 69 (e.g., part number 39-701, distributed by Gray Hill, Inc.) located on the underside of the controller 3 are push button switches that have a plastic actuator stem which aligns with the identification bumps 80 on the cover plate 87 of a pump body to selectively operate some, or all, of the switches. The switches are wired to a programmable logic device (hereinafter referred to as a PLD) which detects the pattern of closed and open switches. A PLD suitable for use with the illustrative embodiment is a Xilinx™ programmable logic device distributed by Xilinx, Inc. of San Jose, Calif. The PLD and the remainder of the circuitry is powered by a conventional power supply which may have a safety mechanism, such as a crowbar circuit, that shuts the unit down in the event of a power surge.

Figure 14:
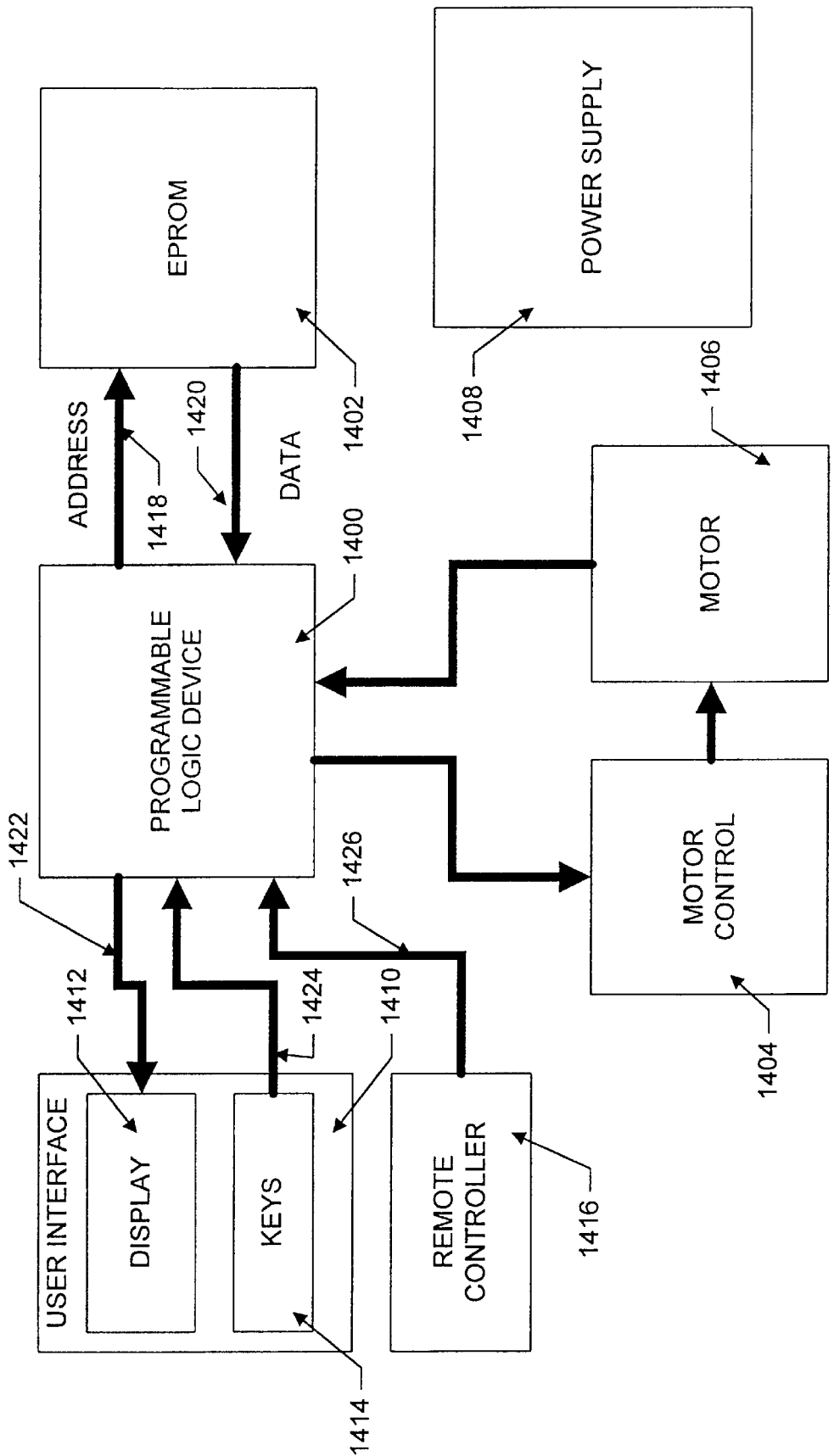
FIG. 14 is a block schematic diagram of the controller electronics.

The general layout of the controller electronics is illustrated in FIG. 14. The main elements are the programmable logic device 1400, an erasable programmable read only memory (EPROM) 1402, a motor controller 1404, a motor 1406 and a power supply 1408. There is also a user interface 1426 which includes an LED display 1412 and a membrane keyboard 1414. A remote control 1416 can also be used with the controller. The PLD 1400 generates address signals on an address bus 1418 which address signals are applied to the EPROM 1402 and data is returned from the EPROM 1402 to the PLD 1400 on a data bus 1420. The PLD can also control the display driver 1412 by means of leads 1422 and receive data from the keyboard 1414 or remote control 1416 by means of leads 1424 and 1426, respectively.

The PLD 1400 controls the motor 1406 by means of a motor control 1404. The motor control 1404, in turn, generates a current drive which operates motor 1406. The position of motor 1406 is determined by sensors in motor 1406 and returned, via leads 1432, to PLD 1400 in order to provide closed loop motor control.

Figure 8A:
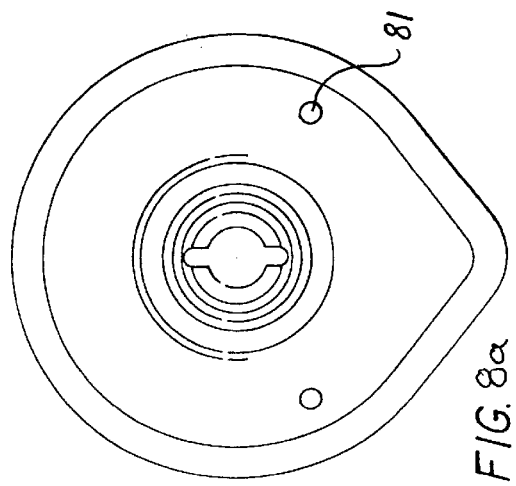
Figure 8D:
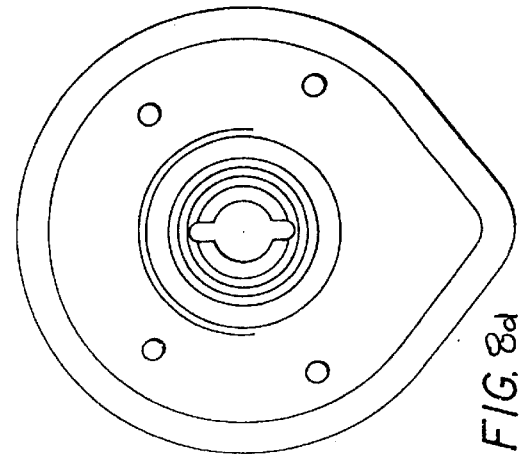

The PLD 1400 is a programmable logic device which electronically reads the pattern of switches which are depressed by the bumps and generates an address word on address bus 1418 which is unique for each switch pattern. In order for the PLD 1400 to detect the presence or absence of a pump body, the pump bodies are arranged so that one of the switches is always depressed when any pump body is present. For example, bump 81 shown in FIG. 8A is present in every bump pattern illustrated in FIGS. 8A–8F. The absence of a pump body in the controller causes the PLD 1400 to control the LED display driver 1412 to generate the display the word "LOAD" on the LED display 27 and to illuminate the "STOP" button 35. This switch is also used for motor safety interlock which will open the return line (not shown) from the motor 1406 should a user open the frame 41 while the controller is in operation.

When one switch is depressed by bump 81, the PLD 1400 generates an address word on bus 1418 based on the positions of the other switches. The address word is, in turn, applied to EPROM 1402 and used to access one of a plurality of lookup tables, permanently programmed into the memory. Each pump body has a dedicated section in the EPROM 1402 where its table is loaded. The EPROM 1402 is addressed by the decoded switch pattern for a particular pump body lookup table.

Figure 15:
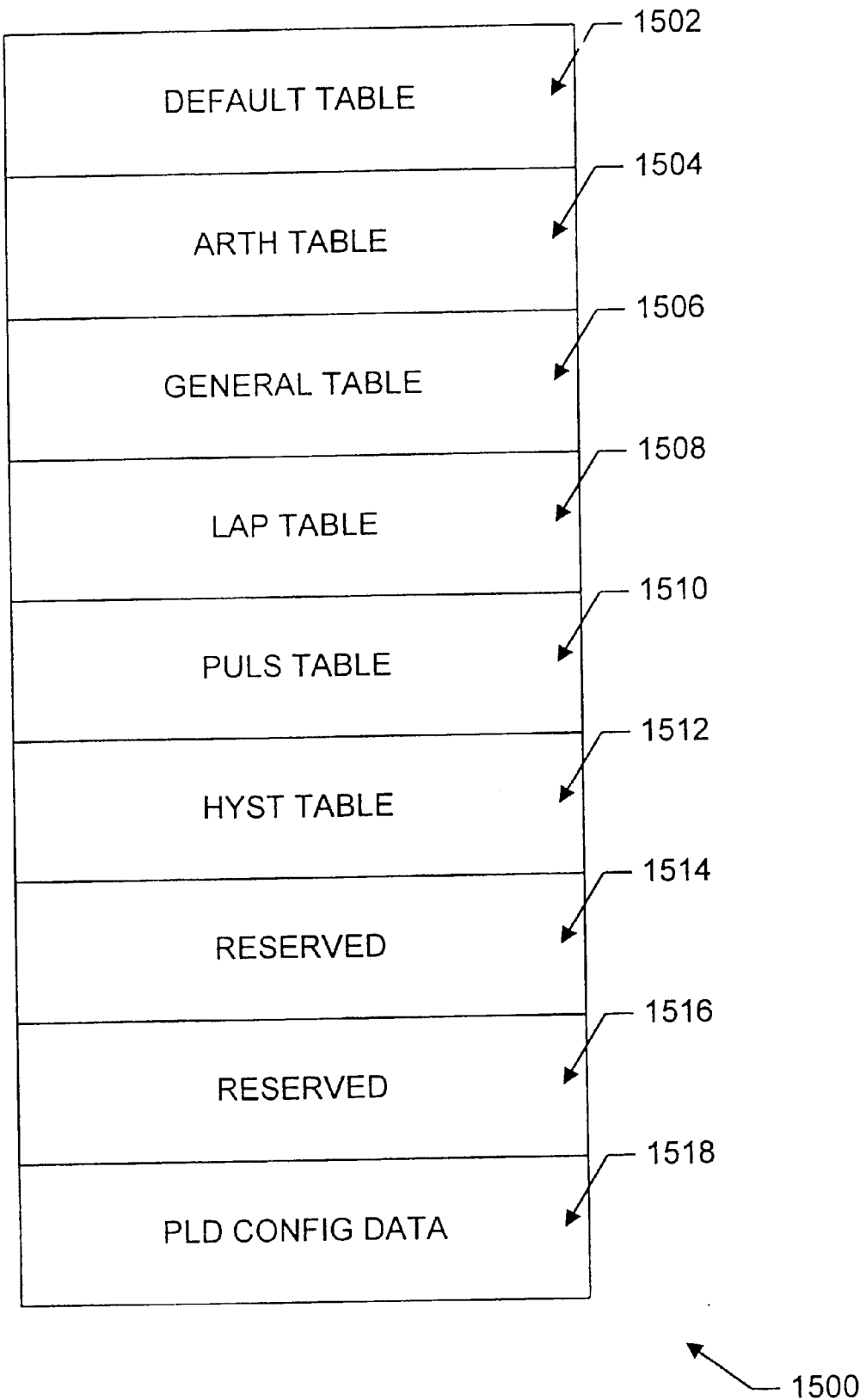
FIG. 15 is a schematic diagram of an illustrative layout of the ROM memory.

The general layout of the EPROM 1402 is shown in FIG. 15. The EPROM 1500 is divided into eight—2000 hex byte blocks 1502–1516 in the lower half of the EPROM with the top half 1518 being reserved for PLD configuration data. As shown, illustrative tables are illustrated for an arthroscopic procedure (table 1504); a general procedure (table 1506); a laparoscopy procedure (table 1508); a procedure requiring a pulsing output (table 1510); a hysteroscopic procedure (table 1512) and two tables reserved for future procedures (tables 1514 and 1516). When the controller is first powered on, the PLD 1400 is programmed to force the address bus 1418 to address certain memory locations which will cause the display 27 to have the "**" test pattern displayed followed by the word "LOAD". The test pattern "**" and the word "LOAD" is programmed into all the pump body tables 1502–1516 at the same position within each table. Therefore, no matter which table is selected by the switch pattern, the test pattern and "LOAD" word will always be generated. If for any reason an incorrect low address is generated, the error pattern "----" will be displayed as the default table 1502 is blank. After the controller start routine has finished, the address bus 1418 will be released with the word "LOAD" displayed in display 27 and the controller waits for the first pump body to be loaded.

Once a pump body is loaded, the address bus 1418 is directly accessed by the switches through a decoding circuit permanently programmed into the PLD 1400. In particular, loading a pump body and closing the frame 41 will cause a combination of switches 69 to be activated. Three of the four switches directly control address lines in the address bus 1418 and will access that start of one of the seven tables 1504–1516. Each table corresponds to one of the pump body types and includes pump body parameters pertinent to a particular pump body, such as, for example, the surgical application, a default starting pressure, and a pressure scale. Each table, in turn, is arranged the same way. The first memory location in each table contains the name of the corresponding pump body using a four letter abbreviation. Following the name is an address offset of the default and maximum speeds for the pump body from the first address of that table. The pressure scale parameters stored in the look up tables may include pressure units to be used for each pump body. For example, the pressure units for an arthroscopic, laparoscopic, or hysteroscopic application may be millimeters of mercury whereas the units for a pulsatile application for example, may be designated as "low," "medium," and "high." The pressure scale parameters also may include a maximum and minimum output pressure value for each of the pump bodies based on the intended medical procedure. An arthroscopic application, for example, may require pressures in the range from 70 millimeters of mercury to 300 millimeters of mercury.

A word representing the surgical procedure is sent to LED display drivers to cause a light emitting diode display on the front face of the unit to display the information pertinent to the pump body being used. For example, the LED display might generate the word "ARTH" for an arthroscopic procedure, the word "LAP" for a laparoscopic procedure, etc. The PLD then waits for the user to depress the confirm procedure button 37 (FIG. 2) on the control panel. Until the confirmation button is pressed, the unit will not proceed.

More specifically, a specially programmed portion of the PLD 1400 is driven by a clock. The PLD 1400, in turn, causes data stored in the lookup tables to be applied to the display driver 1412 using a write pulse derived within the PLD. Each lookup table has 16 bytes of data. The display driver 1412 operates with two words, an upper word and a lower word. The first ten bytes of data in the selected lookup table in EPROM 1402 are output to the display driver 1412 using the write pulse. First the lower display word is selected and 5 bytes are output, the upper word is then selected After the 10 bytes of display data have been sent, 2 bytes for the default memory location, which is an offset from the starting location of the table, low byte first, then 2 bytes which represent the length of the table (highest table entry) are output to the PLD 1400.

When the PLD detects depression of the confirmation button, it controls the LED display to display the default starting pressure value retrieved from the ROM. In particular, data at the default memory location is loaded. For example, 10 bytes are sent to the display driver 1412 for the default pressure. The next 2 bytes retrieved set the motor speed for that pressure. The "STOP" button then is illuminated and the "START" button 33 is not illuminated. The controller is now ready to start the internal electric motor. The motor is actually started when the user depresses the "START" button.

When the "START" button is depressed, the PLD transmits a digital word to a motor controller circuit which controls the motor according to the default starting pressure obtained from the lookup table for the installed pump body. The default starting pressure is also pre-loaded into an up/down counter. The motor controller circuit may, for example, be a commercially-available integrated circuit which that converts the digital signal to a D.C. motor drive current. A motor controller circuit suitable for use with the illustrative embodiment is a Brushless D.C. Motor Controller Circuit, part no. MC3035, distributed by Motorola, Inc. The motor is a three-phase brushless DC motor which has Hall-effect sensors that sense rotor position. The outputs of the sensors are provided to the PLD 1400 for closed-loop speed control.

After the selected pump body has been confirmed to be correct by the user depressing the "CONFIRM PROCEDURE" button, the operation of the unit may be controlled by either the control panel on the face of the unit, or by a remote controller 20 (FIG. 1) that is connected to the unit by a flexible conductive cable 21 which plugs into a receptacle 46 (FIG. 3). A key pad on the remote controller may be any known switching device, such as a conductive membrane-type switch and the remote controller preferably includes a start button, a stop button, an increase pressure button and a decrease pressure button and the switches on the remote controller are connected in parallel with the switches on the controller control panel. Optocouplers (e.g., part no. TIL193 from Texas Instruments of Dallas, Tex.) preferably are included on all electrical leads connecting the remote controller 20 to the controller 3 in order to electrically isolate the remote controller from the power supply in the controller 3. The electrical isolation prevents or mitigates the chances of an attendant who may be holding the remote controller 20 from receiving an electrical shock in the event that an electrical short circuit develops in the controller 3.

During operation, the user can change the rotational speed of the motor by pressing either the increase button 29 or the decrease button 31. The increase and decrease buttons 29 and 31 directly change the RPMs of the motor, thereby changing the output pressure. To that end, when the decrease button 31 is pressed, the PLD responds by decrementing the up/down counter to cause a new EPROM address location to be placed on the address bus 1418. Newly addressed information would then be loaded to the display driver 1412 and the motor control 1404. The PLD also contains comparator circuits which are pre-loaded with the minimum output pressure value. The decremented up/down counter value is compared to minimum output pressure. If the decreased value is greater than or equal to the minimum pressure value, the decreased value is transmitted to the motor controller to reduce the rotational speed of the motor, thereby decreasing the pump output pressure. In addition the decreased value is provided to the LED driver circuitry to cause the LED display to generate a display corresponding to the new value. Alternatively, if the decreased value is less than the minimum pressure value, the counter is deselected. A similar routine is followed in the case where the user presses the increase button 29.

Figure 7:
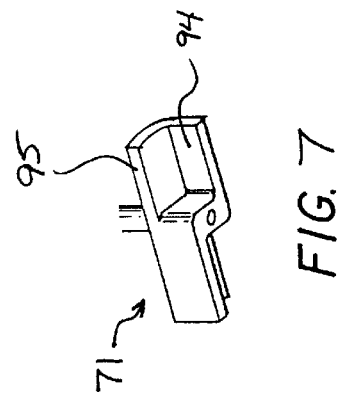
FIG. 7 is a detailed illustration of the S-shaped paddle.

Another important interface between the installed pump body 5 and the controller 3 is the connection of drive power from the electric motor within the controller to the pumping mechanism of the disposable pump. Once the frame 41 has been closed and the cover plate 87 of pump body 5 is pressed against the underside surface 68 of the controller, the protruding end of the pump drive rod 82 will be aligned to come into contact with the S-shaped paddle 71 of the controller. Referring to FIGS. 5, 6 and 7, once the motor 76 is energized, motor shaft 73 and S-shaped paddle 71 will rotate. Upon rotation of the paddle, the end of the pump drive rod 82 will come into contact with recessed edge 94 of the paddle 71. As the paddle then rotates under the power of the electric motor, the drive rod 82 of the pump body 5 will be moved to generate pumping action within the pump.

Another important interface between the cover plate 87 and the underside 68 of the controller 3 is secure contact between their surfaces. Upon closure of the frame 41 by engaging lip 60 with lip 65 of the latch 39, the cover plate 87 of pump body 5 will come into contact with the underside surface 68 of the controller housing 25. With the top edge surface 56 of frame 41 maintaining an upward force against the bottom of the pump bowl body locating ridge 83, the pump body 5 will be securely attached to the controller. Flexible pads 52 insure that there is a complete interface between the surfaces. The upstanding ridge on pads 52 are intended to crush partially or completely to provide this interface.

During operation, if fluid seepage were to occur from the cover plate 87 of the pump body 5, a firm interface with the bottom of the controller would prevent the fluid from draining away quick enough. A buildup of fluid between the cover plate 87 and the bottom of the controller may cause fluid to enter the switches 69 and the seal (not shown) around the motor shaft 73 and damage controller components. To avoid this potential problem, several channels 90 are recessed into the underside of the controller housing 68 to provide space for fluid to escape and drain away safely from the back of the controller. Additionally, elastomeric boots (not shown) may be placed over switches 69 to protect them from the potentially damaging effects of a fluid leak.

Figure 9A:
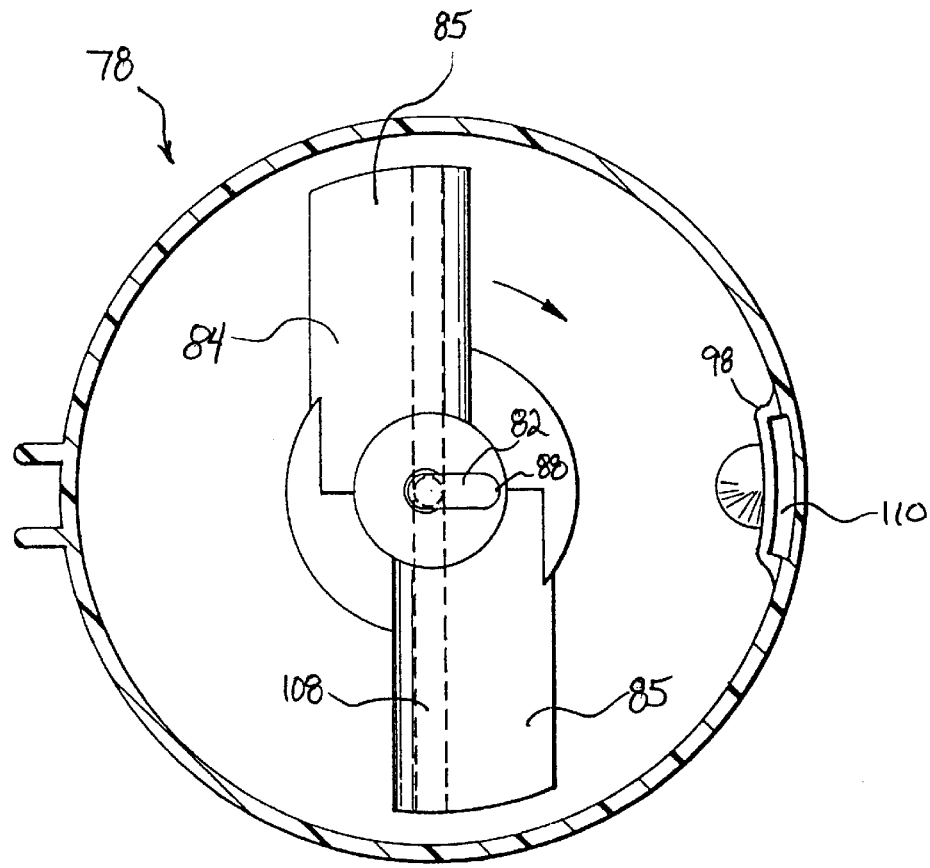
FIG. 9A is a top cut-away view of the laparoscopy pump body.
Figure 9B:
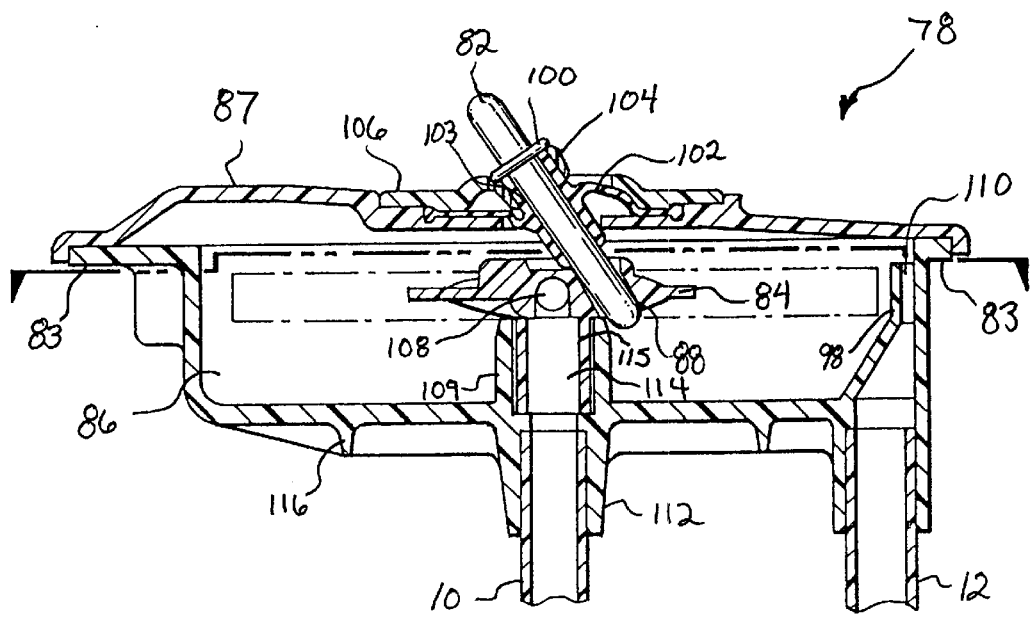
FIG. 9B is a side view of the laparoscopy pump body.

The disposable pump body for use with laparoscopic procedures is shown in FIGS. 9A and 9B. The incoming fluid line 10 joins the pump body at inlet 112 which is in fluid communication with the hollow shaft 115 of the T-shaped rotating impeller 84. Fluid travels through the hollow shaft, then radially outward through conduits 108 which pass through vanes 85. A cylindrical receptacle 109 is molded into the bottom wall of the pump body and holds the hollow shaft 114 of the impeller 84. The use of low friction plastic materials at the bearing surfaces of the shaft 114 and the receptacle 115 and the presence of liquid between the contact surfaces prevents the bearing from seizing during use. The entire pump body and cover plate are made from the same material as the bearing surfaces.

Liquid exits the conduits 108 radially from the spinning impeller which acts as a centrifugal pump and develops a pressure within the pumping chamber 86 which pressure is related to the length of the vanes 85 and the rotational speed of the spinning impeller and the additive affect of turbulence. Pressurized liquid exits the pumping chamber 86 through outlet 110 positioned on the interior of the outside wall of the pumping chamber. As will be discussed in more detail below, an interior wall 98 is molded into the pump body wall which insures that the liquid outlet 110 is positioned near the cover plate 87 of the pumping chamber 86 when the pump body 5 is mounted in the controller. The position of the fluid outlet advantageously permits air to be purged from the pump body during an inventive priming procedure.

The top of the pumping chamber 86 is sealed by a cover plate 87 that is of the same material as the pumping chamber and is joined to the pump chamber by ultrasonic welding or by adhesive.

The pump drive mechanism must pass through the cover plate 87 to spin the impeller 84 in a manner that preserves the liquid tight integrity of the entire pump bowl. A pump drive rod 82 passes through a flexible diaphragm 102 that covers an opening at the center of the cover plate 87. The diaphragm 102 is positioned over the hole in the cover plate 87 and is captured against the top surface of the cover plate by flange 106 which is bonded to the top of the cover plate 87 by adhesive or ultrasonic welding. The diaphragm 102 is compressed between the top surface of the cover plate 87 and the flange.

The drive rod 82 passes through a cylindrical sleeve 103 integrally molded into the diaphragm and engages a hole 88 in the impeller 84 as shown in FIG. 9B. A collar 104 encircles the sleeve 103 of the diaphragm to maintain the sleeve in secure contact with the surface of the drive rod 82, thereby forming a liquid tight seal. An annular rib 100 on the drive rod butts up against the top of the collar 104 to prevent the collar 104 from sliding off the sleeve 103 during shipping, and to prevent the diaphragm 102 from being urged upwardly by the pressure developed in the pump body during activation.

The drive rod 82 transmits power from the revolving S-shape paddle 71 of the controller 3 to the rotating impeller 84 within the pump chamber 86. When the pump body is secured to the undersurface of the controller 3, the impeller 84 and the S-shape paddle 71 share a common axis of rotation. However, the drive rod connects with the impeller and S-shape paddle at points that are offset from the axis of rotation, such that the drive rod is skewed across the axis of rotation. Therefore, as the S-shape paddle rotates under power from the motor, the drive rod rotates, causing the impeller to rotate. Because the drive rod moves in a nutating motion, rather than rotates within the sleeve 103 of the diaphragm 102, the liquid tight connection between the surfaces can be maintained more readily as the sealing surfaces do not move relative to each other. The diaphragm 102 can be formed with a cross-sectional wave shape (for example, as an S-shape) to reduce stress as the diaphragm flexes due to nutation of the drive rod 82. The wave shape would be compressed and oppositely tensioned as rotation occurs. Friction is reduced at this connection through the use of low friction materials in the components, combined with the presence of liquid in the drive rod/impeller connection when the pumping chamber 86 is filled with liquid.

Orienting the shaft 82 at a thirty degree angle relative to the longitudinal axis of the motor shaft 73 has yielded satisfactory performance results. Consequently, as shown in FIG. 7, sloped shaft surface 94A preferably also slopes at a thirty degree angle to contact the outer surface of the shaft 82. A searing flange 71a also may be included on the paddle 71 to prevent the shaft 82 from losing contact with sloped surface 94A.

In the preferred embodiment, there are no one way fluid valves to prevent the retrograde of liquid through the system. The fluid path from the reservoir bags 8, through the pump 5, tubing 12, and handpiece 16 therefore may be considered as forming an unobstructed liquid flow path when the system is operating. Accordingly, any undesirable excessive pressure build up in a body cavity will decrease the rate that irrigation liquid enters that cavity.

Figure 12A:
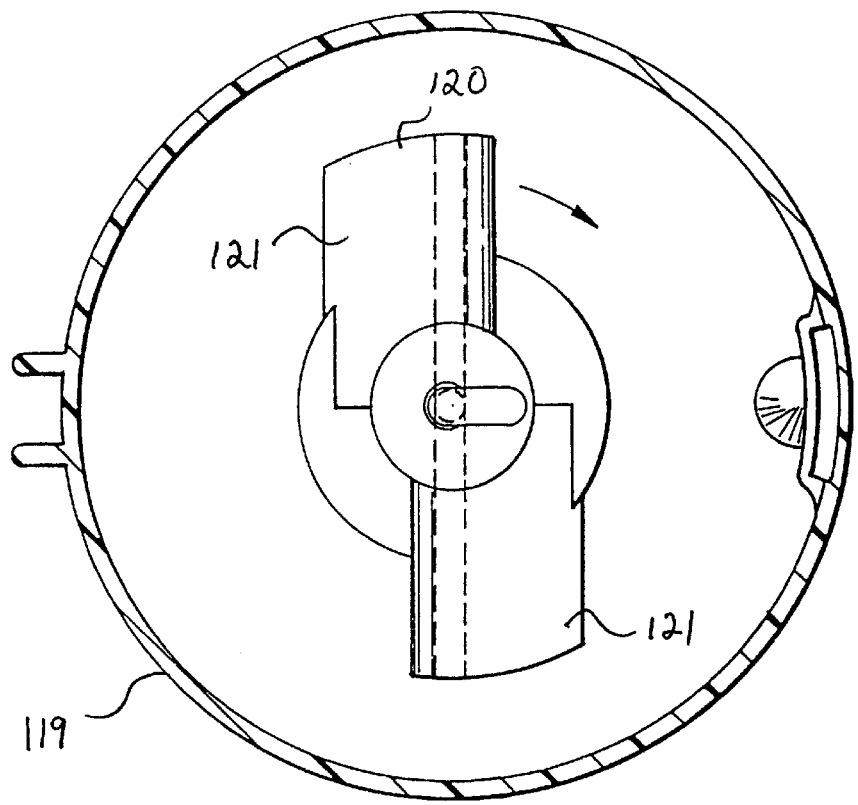
FIG. 12A is a top cut-away view of the arthroscopy pump body.
Figure 12B:
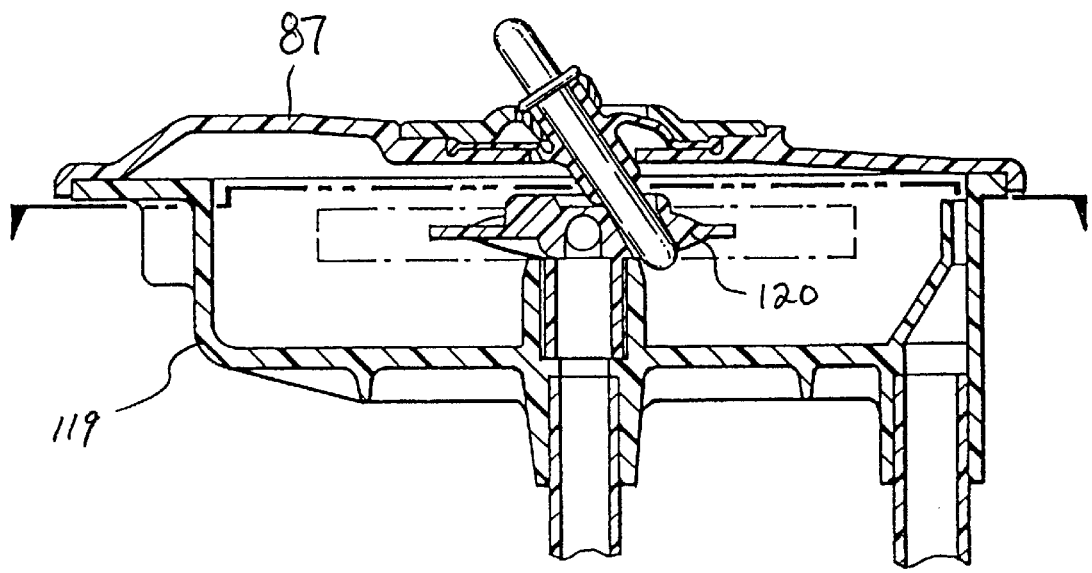
FIG. 12B is a side view of the arthroscopy pump body.

Pump bodies designed especially for various other medical procedures utilizing the overall design embodiment are shown in FIGS. 12A, 12B and 13A, 13B. The pump body illustrated in FIGS. 12A and 12B is designed for use in arthroscopic procedures. It is similar in shape, design and dimension to the laparoscopic pump body described in relation to FIGS. 9A and 9B. The arthroscopic pump body 119 employs an impeller 120 having shorter vanes 121 than the impeller 84 used with the laparoscopic pump body described above. This design change optimizes pump performance and utilizes reduced pressures that are desired for arthroscopic use. Since the fluid pressure developed by the pump is related to the vane length and the rotation speed, for a given pump body, the pressure developed by the pump depends on the rotational speed. However, to optimize the desired output pressure range to rotational speed values which are comfortably within the rotational speed ranges of the motor, it is desirable to use pump bodies with different vane lengths. With a longer vane length, higher pressures can be generated without requiring that the motor be run a very high rotational speeds. However, although the pump body 119 is optimized for a particular medical procedure, the cover plate 87 and the locating bowl flange ridge (the exterior of the pump body in this case) are the same as for all pump bodies. These fixed dimensions allow the different pump bodies to be used interchangeably with the same controller unit.

Figure 10:
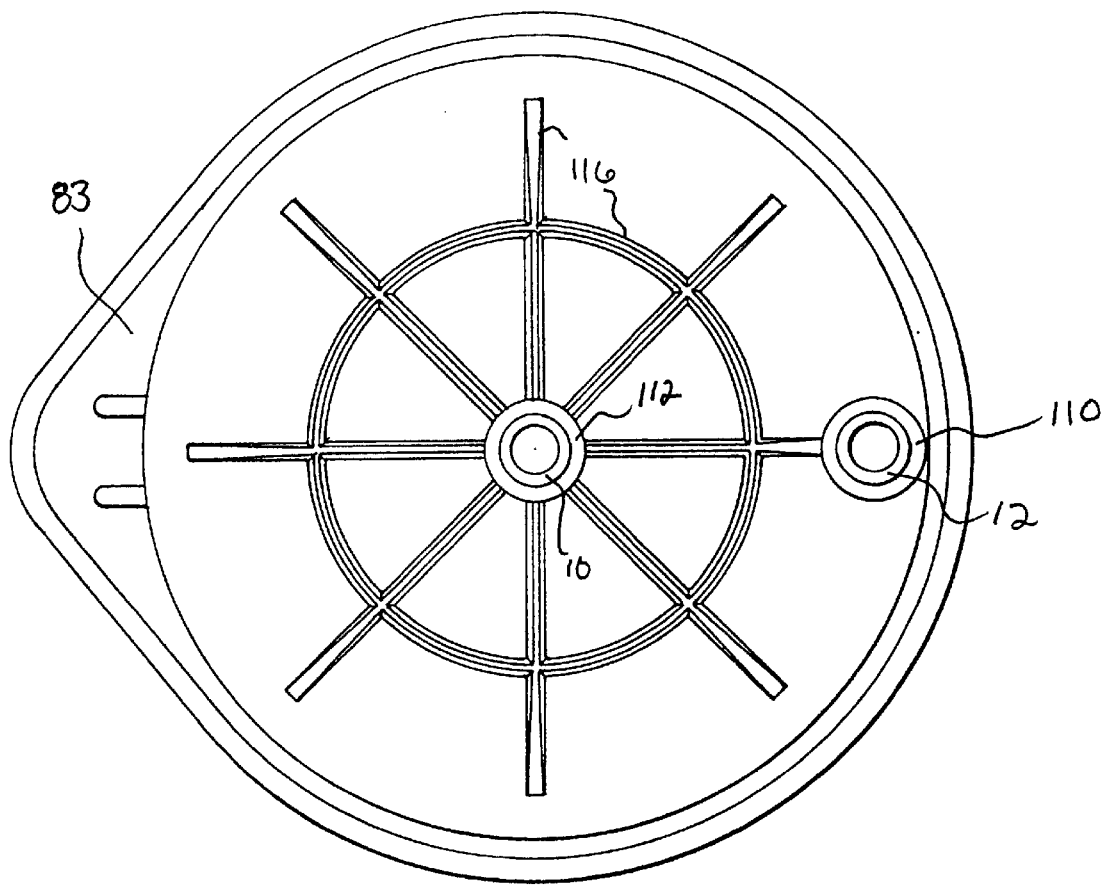
FIG. 10 is a bottom view of a pump body generally.

FIG. 10 is a bottom view of the laparoscopic and arthroscopic pump bodies. A set of ribs 116 of increased thickness are formed into the wall during molding to provide structural support to the bottom of the pump body. The added structural support prevents pressure variations in the pump output pressure caused by flexure of the bottom wall when the pump body is pressurized during use. The added structural support minimizes flexing of the entire assembly to prevent it from dislodging from the paddle.

Figure 13A:
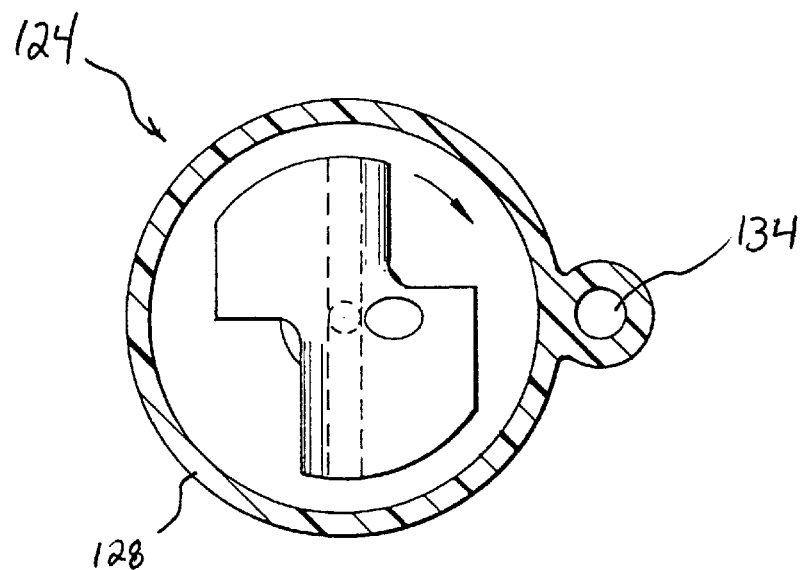
FIG. 13A is a top cut-away view of the hysteroscopy pump body.
Figure 13B:
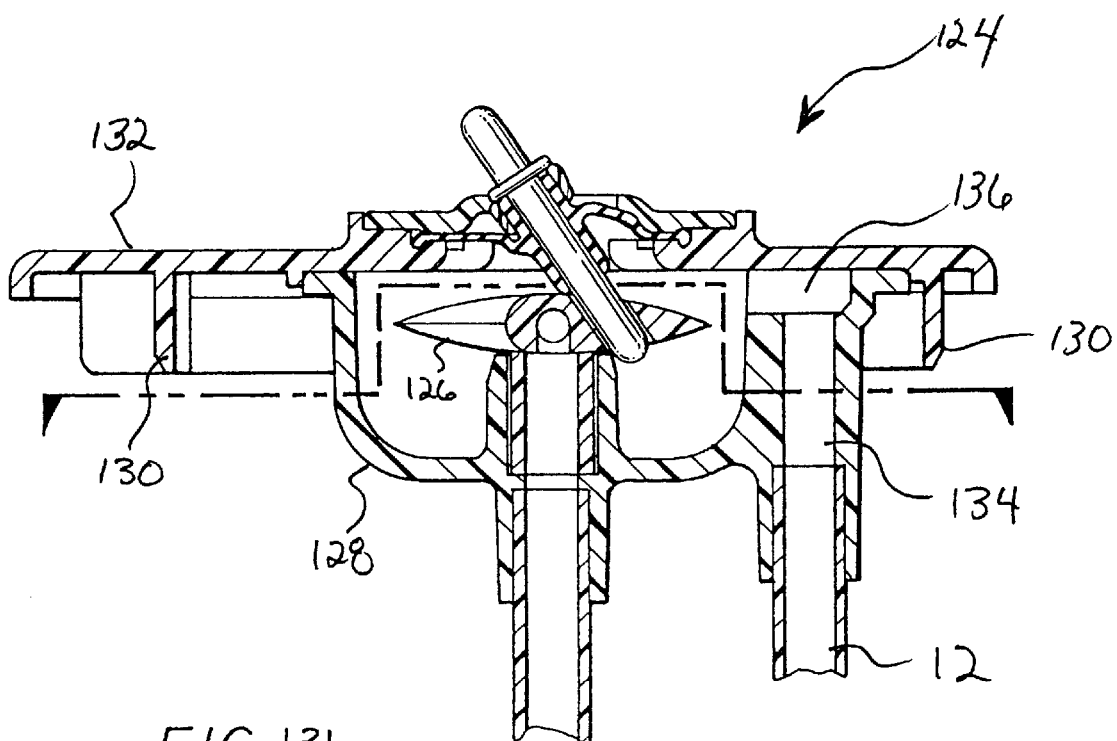
FIG. 13B is a side view of the hysteroscopy pump body.

In addition, pump bodies may be optimized in other ways for particular medical procedures. The pump body 124 intended for hysteroscopic use is shown in FIGS. 13A and 13B. Pump 124 used for hysteroscopic procedures employs a pump chamber 128 that is not only substantially smaller in diameter than those used for the previously described laparoscopic and arthroscopic procedures, but also has a different shape. In particular, the smaller pump chamber 128 has a hemispherical shape which helps reduce the amount of air bubble formation that would otherwise occur (in the larger pump chamber) when operating at the lower pressures required in a hysteroscopic procedure. Excessive air bubbles could cause substantial pressure variations within the pump chamber, possibly adversely affecting performance of the pump. The hemispherical shape of the pump chamber also helps to reduce fluid stagnation in the pump chamber and the small size limits the maximum pressure to a safe limit. The substantially smaller size requires a lesser volume of priming solution that may be clinically controlled.

Though the pump chamber 128 has a smaller diameter than the other pump bodies described above, the cover plate 132 of the hysteroscopic pump body 124 is dimensioned to maintain interchangeability within the frame 41 of controller 3. The overall diameter of the cover plate 132 is the same as the lid used with other pump bodies. Furthermore, the cover plate 132 employs a downward extending locating ridge 130 that corresponds to the external diameter flange of the pump bodies used in the other larger pump bodies described above. Therefore, the surface of the locating ridge 130 fits securely within the circular edge 58 of the frame 41. All other characteristics of the hysteroscopic pump body are similar to those described in connection with the laparoscopic pump body.

Figure 11:
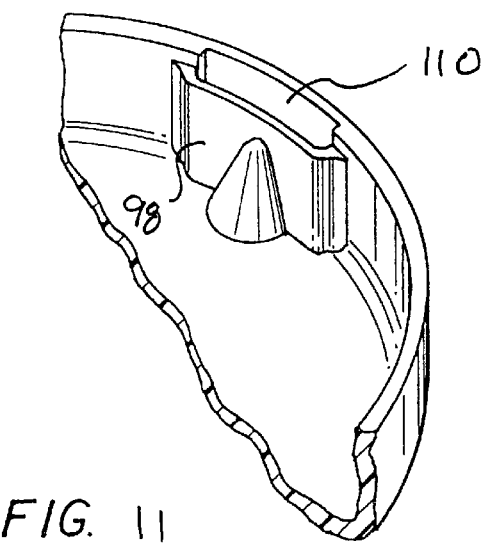
FIG. 11 is a detail view of the outlet of the pump body generally.

In accordance with one aspect of the invention, all pump bodies are designed for automatic priming. In particular, during the priming procedure, air is purged from the pump body. FIG. 11 shows a detail of the elevated outlet 110 employed in the pump chambers of the laparoscopic and arthroscopic pump bodies. Wall 98 on the interior of the pump chamber ensures that fluid exits only from the very top of the chamber through outlet 110. In the same manner, the hysteroscopic pump body also employs an elevated outlet 136 as shown in FIG. 13B. Fluid discharged from the pump then travels down through outlet port 134 then through the outlet line 12. The elevated outlet position on the edge of the pump chamber of the several pump bodies is particularly effective in eliminating air bubbles when priming the pump chamber with fluid during the loading procedure that is described in detail below.

To load a pump body for use with the controller, the user first opens the frame 41 by depressing the release latch 39 allowing the frame 41 to drop to the open position illustrated in FIG. 5. The user then selects the appropriate pump body for the intended procedure and inserts the pump in the frame by navigating the inlet and outlet lines through the opening 57 of frame 41. The pump body may then be lowered into the frame so that the pump chamber falls within the round edge 58 of the frame and body ridge 83 of the pump body contacts surface 56 of the frame 41. When properly installed the outlet line of the pump body will be oriented towards the back of the controller near the hinge 54 of the frame as shown in FIG. 5. The open position of the door and the corresponding angular orientation of the pump body automatically positions the fluid outlet at the highest point of the pump chamber as is shown in FIG. 5. Once the pump body is joined to an irrigation reservoir that is higher than the pump body, liquid travels under the force of gravity to the pump body and enters through the inlet line 10 at the center of the pump chamber. The liquid rises through the impeller 84 and fills the chamber 86 starting from the lowest point. As the fluid level rises within the pump chamber 86, air is displaced out of the chamber as it is displaced by the rising liquid. With the outlet positioned at the highest point in the chamber the air within the chamber has an outlet through which it can be displaced. All air bubbles are effectively purged from the chamber 86 so that no air bubbles remain trapped in the chamber 86 once the chamber has been completely filled with liquid. This process automatically and effectively primes the pump chamber with liquid with minimum effort by the user.

Once the pumping chamber has been primed, the frame 41 is closed upward and engaged with the latch 39. Upon closure, the energized controller will identify which type of pump body has been installed by recognizing the sequence of depressed switches (engaged by the sequence of bumps on the top of the cover plate pump body) and controller operation can be initiated as described above.

It should be understood that while the foregoing description of the invention is intended to be diagrammatic and illustrative only, other embodiments, modifications and uses may be apparent to those skilled in the art without departing from its spirit.

Having thus described the invention what I desire to claim is secured by Letters Patent is:

1. A disposable pump mechanism connectible to an irrigation fluid source, the pump mechanism being for use with a non-disposable drive mechanism and comprising:

a pumping mechanism configured to produce an irrigation fluid output particularly suited for a predetermined medical procedure;

a housing which is adapted to mate with the drive mechanism and does not depend on the predetermined medical procedure for which the pump mechanism is suited; and identifying indicia unique to the predetermined medical procedure comprising a pattern of bumps, which identifying indicia can be sensed by the drive mechanism.

2. The pump mechanism of claim 1 wherein the identifying indicia is located on the surface of the housing.

3. The pump mechanism of claim 2 wherein the housing has a cover plate and the pattern of bumps are located on the cover plate.

4. The pump mechanism of claim 1 wherein the pumping mechanism comprises a centrifugal pump.

5. The pump mechanism of claim 4 wherein the centrifugal pump comprises a nutating drive rod.

6. The pump mechanism of claim 5 wherein a flexible diaphragm comprises part of the housing and wherein the nutating drive rod extends through the diaphragm.

7. The pump mechanism of claim 6 wherein the flexible diaphragm has a cross section in the form of a double S.

8. The pump mechanism of claim 1 wherein the housing has a vent for purging air from the housing.

9. The pump mechanism of claim 1 wherein the vent is located in a position which permits substantially complete removal of air from the housing.

10. The pump mechanism of claim 9 wherein the housing has an inlet and an outlet and the vent is located in the outlet.

11. A disposable pump mechanism connectible to an irrigation fluid source, the pump mechanism being for use with a non-disposable drive mechanism and comprising:

a centrifugal pump having a rotating vane and a housing wherein both the rotating vane and the housing are sized to produce an irrigation fluid output particularly suited for a predetermined medical procedure;

a cover plate attached to the pump housing which is adapted to mate with the drive mechanism and does not depend on the predetermined medical procedure for which the pump is suited; and a pattern of identifying bumps on the cover plate wherein the pattern is unique to the predetermined medical procedure, which bumps can be sensed by the drive mechanism.

12. The pump mechanism of claim 11 wherein the centrifugal pump comprises a nutating drive rod for rotating the rotating vane.

13. The pump mechanism of claim 12 wherein the drive rod is oriented at a thirty degree angle relative to the axis of the centrifugal pump.

14. The pump mechanism of claim 12 wherein a flexible diaphragm comprises part of the pump housing and wherein the nutating drive rod extends through the diaphragm.

15. The pump mechanism of claim 14 wherein the flexible diaphragm has a cross section in the form of a double S.

16. The pump mechanism of claim 11 wherein the pump housing has a vent for purging air from the housing.

17. The pump mechanism of claim 16 wherein the vent is located in a position which permits substantially complete removal of air form the pump housing.

18. The pump mechanism of claim 17 wherein the pump housing has an inlet and an outlet and the vent is located in the outlet.

19. The pump mechanism of claim 18 wherein the pump housing is substantially circular and the inlet is located at the center of the housing and the outlet is located at the edge of the housing.

20. The pump mechanism of claim 19 wherein the pump housing has reinforcing ribs on substantially flat areas.

21. The pump mechanism of claim 20 wherein the shape of the housing is suited for one of the plurality of medical procedures.

22. The pump mechanism of claim 11 wherein the irrigation source, non-disposable drive mechanism and pump form an unobstructed liquid flow path from an irrigation site to the irrigation source.

* * * * *

UNITED STATES PATENT AND TRADEMARK OFFICE
CERTIFICATE OF CORRECTION

PATENT NO. : 6,077,246
DATED : June 20, 2000
INVENTOR(S) : Kullas et al.

It is certified that error appears in the above-identified patent and that said Letters Patent are hereby corrected as shown below:

Column 16, Line 7, change the word "form" to "from"

Signed and Sealed this

Third Day of April, 2001

Attest:

NICHOLAS P. GODICI

*Attesting Officer*     *Acting Director of the United States Patent and Trademark Office*